United States Patent
Hauel et al.

(10) Patent No.: US 7,189,743 B2
(45) Date of Patent: *Mar. 13, 2007

(54) PRODRUGS OF 1-METHYL-2-(4-AMIDINOPHENYLAMINOMETHYL)-BENZIMIDAZOL-5-YL-CARBOXYLIC ACID-(N-2-PYRIDYL-N-2-HYDROXYCARBONYLETHYL)-AMIDE

(75) Inventors: Norbert Hauel, Schemmerhofen (DE); Florian Colbatzky, Stafflangen (DE); Ulrich Busch, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/056,029

(22) Filed: Feb. 11, 2005

(65) Prior Publication Data

US 2005/0137233 A1     Jun. 23, 2005

Related U.S. Application Data

(63) Continuation of application No. 10/631,645, filed on Jul. 31, 2003, now Pat. No. 6,900,229.

(60) Provisional application No. 60/405,239, filed on Aug. 22, 2002.

(30) Foreign Application Priority Data

Aug. 2, 2002    (DE) ................ 102 35 639

(51) Int. Cl.
    *A61K 31/44*    (2006.01)
(52) U.S. Cl. ..................... 514/338; 514/339; 546/270.1
(58) Field of Classification Search ............. 546/270.1; 514/338, 339
    See application file for complete search history.

(56) References Cited

U.S. PATENT DOCUMENTS

| | | | |
|---|---|---|---|
| 6,087,380 A | 7/2000 | Hauel et al. | |
| 6,414,008 B1 | 7/2002 | Hauel et al. | |
| 6,469,039 B1 | 10/2002 | Hauel et al. | |
| 6,710,055 B2 | 3/2004 | Hauel et al. | |
| 6,900,229 B2 * | 5/2005 | Hauel et al. | 514/338 |

FOREIGN PATENT DOCUMENTS

WO    WO 98/37075 A1    8/1998

OTHER PUBLICATIONS

Hauel, N., et al; "Disbustituted Bicyclic Heterocycles, The Preparation Thereof and their Use as Pharmaceutical Compositions"; U.S. Appl. No. 10/192,041, filed Jul. 10, 2002.

* cited by examiner

*Primary Examiner*—Amelia A. Owens
(74) *Attorney, Agent, or Firm*—Michael Morris; Mary-Ellen M. Devlin; Thomas Blankinship

(57) ABSTRACT

The present invention relates to new compounds of general formula

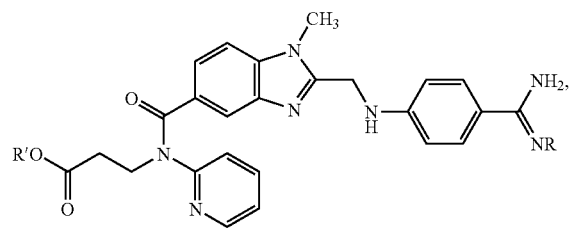

(I)

having thrombin-inhibiting activity. Exemplary are:
1-Methyl-2-[4-(N-hydroxyamidino)-phenylaminomethyl]-benzimidazol-5-yl-carboxylic acid-(N-2-pyridyl-N-2-ethoxycarbonylethyl)-amide, and
1-Methyl-2-[4-(N-methoxycarbonylamidino)-phenylaminomethyl]-benzimidazol-5-yl-carboxylic acid-(N-2-pyridyl-N-2-hydroxycarbonylethyl)-amide.

18 Claims, No Drawings

PRODRUGS OF 1-METHYL-2-(4-AMIDINOPHENYLAMINOMETHYL)-BENZIMIDAZOL-5-YL-CARBOXYLIC ACID-(N-2-PYRIDYL-N-2-HYDROXYCARBONYLETHYL)-AMIDE

RELATED APPLICATIONS

This application is a continuation of U.S. patent application Ser. No. 10/631,645, which was filed on Jul. 31, 2003, now U.S. Pat. No. 6,900,229, and which is an application claiming the benefit under 35 USC 119(e) of U.S. Provisional Patent Application No. 60/405,239, which filed on Aug. 22, 2002.

DESCRIPTION OF THE INVENTION

The present invention relates to new compounds of general formula

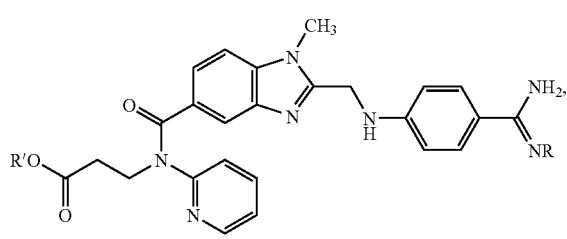

(I)

the tautomers and the salts thereof, particularly the physiologically acceptable salts thereof with inorganic or organic acids or bases, which have valuable properties.

The compounds of general formula I are prodrugs of the thrombin-inhibiting compound 1-methyl-2-(4-amidinophenylaminomethyl)-benzimidazol-5-yl-carboxylic acid-(N-2-pyridyl-N-2-hydroxycarbonylethyl)-amide (II),

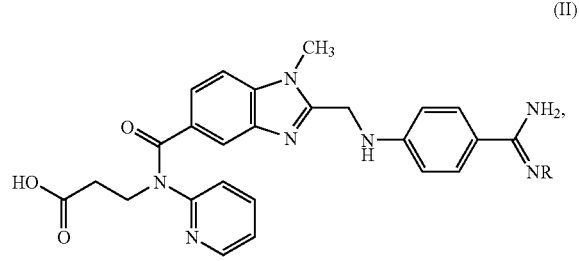

(II)

which is already known from WO 98/37075, U.S. Pat. No. 6,087,380, U.S. Pat. No. 6,414,008, U.S. Pat. No. 6,469,039, and U.S. Pat. No. 6,710,055. PCT Application No. WO 98/37075 entered the national stage in the United States on Feb. 18, 1998, and subsequently issued as U.S. Pat. Nos. 6,087,380, 6,414,008, 6,469,039, 6,710,055. The prodrugs according to the invention are particularly suitable for subcutaneous administration as they are well tolerated after subcutaneous injection, and in particular do not produce any local intolerance at the injection site when administered subcutaneously.

Thus, the present application relates to the new compounds of the above general formula I, the tautomers and the salts thereof as well as the preparation thereof, the pharmaceutical compositions containing the pharmacologically effective compounds and the use thereof.

In the above general formula I a) R' denotes a hydrogen atom and R denotes a methoxycarbonyl group or b) R' denotes a hydrogen atom or a C1–6-alkyl group and R denotes a hydroxy group.

The alkyl groups which contain more than 2 carbon atoms mentioned in the above definition also include the branched isomers thereof such as for example the isopropyl, tert-butyl and isobutyl group.

Preferred compounds of general formula I are those wherein a) R' denotes a hydrogen atom and R denotes a methoxycarbonyl group or b) R' denotes a hydrogen atom or a C1–3-alkyl group and R denotes a hydroxy group, the tautomers and the salts thereof.

The compound 1-methyl-2-[4-(N-hydroxyamidino)-phenylaminomethyl]-benzimidazol-5-yl-carboxylic acid-(N-2-pyridyl-N-2-ethoxycarbonylethyl)-amide, the tautomers and the salts thereof, particularly the physiologically acceptable salts thereof, are particularly preferred.

Particularly preferred salts are the maleate, the hydrochloride and the methanesulphonate of the compound 1-methyl-2-[4-(N-hydroxyamidino)-phenylaminomethyl]-benzimidazol-5-yl-carboxylic acid-(N-2-pyridyl-N-2-ethoxycarbonylethyl)-amide.

Another particularly preferred compound is 1-methyl-2-[4-(N-methoxycarbonylamidino)-phenylaminomethyl]-benzimidazol-5-yl-carboxylic acid-(N-2-pyridyl-N-2-hydroxycarbonylethyl)-amide, the tautomers and the salts thereof, particularly the physiologically acceptable salts thereof.

Particularly preferred salts are the maleate, the methanesulphonate and the sodium salt of the compound 1-methyl-2-[4-(N-methoxycarbonylamidino)-phenylaminomethyl]-benzimidazol-5-yl-carboxylic acid-(N-2-pyridyl-N-2-hydroxycarbonylethyl)-amide.

The new compounds may be prepared by methods known per se, for example by the following methods:

A. In Order to Prepare a Compound of General Formula I wherein R Denotes a Hydroxy Group:

Reacting a compound of general formula

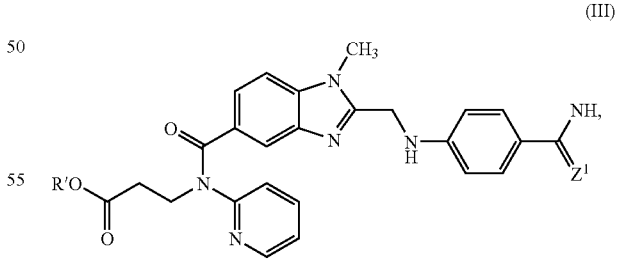

(III)

optionally formed in the reaction mixture, wherein

R' is as hereinbefore defined and

Z1 denotes an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group, with an amine of general formula

 (IV).

The reaction is expediently carried out in a solvent such as methanol, ethanol, n-propanol, water, methanol/water, tetrahydrofuran or dioxane at temperatures between 0 and 150° C., preferably at temperatures between 20 and 120° C., with a compound of general formula III or with a corresponding acid addition salt such as ammonium carbonate, for example.

Compounds of general formula III and the preparation thereof are described for example in WO 98/37075, U.S. Pat. No. 6,087,380, U.S. Pat. No. 6,414,008, U.S. Pat. No. 6,469,039, and U.S. Pat. No. 6,710,055 which have been incorporated herein by reference in their entireties due to the fact that PCT Application No. WO 98/37075 entered the national stage in the United States on Feb. 18, 1998, and subsequently issued as U.S. Pat. Nos. 6,087,380, 6,414,008, 6,469,039, and 6,710,055.

B. In Order to Prepare a Compound of General Formula I wherein R' Denotes Hydrogen:

converting a compound of general formula

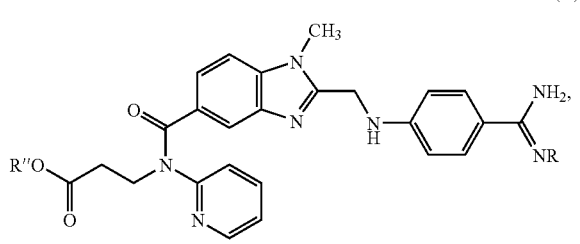

(V)

wherein

R is as hereinbefore defined and

R" denotes a group which can be converted into a carboxyl group by hydrolysis, treatment with an acid or base, thermolysis or hydrogenolysis, into a compound of general formula I wherein R' denotes hydrogen, by hydrolysis, treatment with an acid or base, thermolysis or hydrogenolysis.

Examples of a group which may be converted into a carboxy group include for example a carboxyl group protected by a protecting group, such as the functional derivatives thereof, e.g. the unsubstituted or substituted amides, esters, thioesters, trimethylsilylesters, orthoesters or iminoesters, which may conveniently be converted into a carboxyl group by hydrolysis, the esters thereof with tertiary alcohols, e.g. the tert.-butyl ester, which may conveniently be converted into a carboxyl group by treatment with an acid or thermolysis, and the esters thereof with aralkanols, e.g. the benzyl ester, which may conveniently be converted into a carboxyl group by hydrogenolysis.

The hydrolysis is conveniently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between −10 and 120° C., e.g. at temperatures between ambient temperature and the boiling temperature of the reaction mixture.

If R" in a compound of formula V contains the tert.-butyl or tert.-butyloxycarbonyl group, for example, these may also be cleaved by treatment with an acid such as trifluoroacetic acid, formic acid, p-toluenesulphonic acid, sulphuric acid, hydrochloric acid, phosphoric acid or polyphosphoric acid, optionally in an inert solvent such as methylene chloride, chloroform, benzene, toluene, diethyl ether, tetrahydrofuran or dioxane, preferably at temperatures between −10 and 120° C., e.g. at temperatures between 0 and 60° C., or also thermally, optionally in an inert solvent such as methylene chloride, chloroform, benzene, toluene, tetrahydrofuran or dioxane and preferably in the presence of a catalytic amount of acid such as p-toluenesulphonic acid, sulphuric acid, phosphoric acid or polyphosphoric acid, preferably at the boiling temperature of the solvent used, e.g. at temperatures between 40 and 120° C.

If R" in a compound of formula V contains the benzyl or benzyloxycarbonyl group, for example, these may also be cleaved by hydrogenolysis in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0 and 50° C., e.g. at ambient temperature, and a hydrogen pressure of 1 to 5 bar.

Compounds of general formula V and the preparation thereof are described, for example, in WO 98/37075, U.S. Pat. No. 6,087,380, U.S. Pat. No. 6,414,008, U.S. Pat. No. 6,469,039, and U.S. Pat. No. 6,710,055.

C. In Order to Prepare a Compound of General Formula I wherein R Denotes a Methoxycarbonyl Group:

reacting a compound of general formula

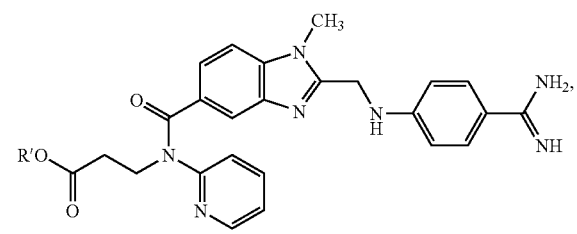

(VI)

wherein

R' is as hereinbefore defined, with a compound of general formula

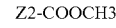 (VII), wherein

Z2 denotes a nucleofugic leaving group such as a halogen atom, e.g. a chlorine, bromine or iodine atom.

The reaction is preferably carried out in a solvent such as methanol, ethanol, methylene chloride, tetrahydrofuran, toluene, dioxane, dimethylsulphoxide or dimethylformamide, optionally in the presence of an inorganic or a tertiary organic base, preferably at temperatures between 20° C. and the boiling temperature of the solvent used.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, acetyl, benzoyl, tert-butyl, trityl, benzyl or tetrahydropyranyl group, a protecting group for a carboxyl group may be a trimethylsilyl, methyl, ethyl, tert-butyl, benzyl or tetrahydropyranyl group and protecting groups for an amino, alkylamino or imino group may be an acetyl, trifluoroacetyl, benzoyl, ethoxycarbonyl, tert-butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is preferably cleaved hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidizing agent such as cerium(IV)ammonium nitrate in a solvent such as methylene chloride, acetonitrile or acetonitrile/water at temperatures between 0 and 50° C., but preferably at ambient temperature.

A 2,4-dimethoxybenzyl group, however, is preferably cleaved in trifluoroacetic acid in the presence of anisole.

A tert-butyl or tert-butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treatment with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under inert gas, or by treatment with a catalytic amount of tris-(triphenylphosphine)-rhodium(I)chloride in a solvent such as aqueous ethanol and optionally in the presence of a base such as 1,4-diazabicyclo[2.2.2]octane at temperatures between 20 and 70° C.

The compounds of general formulae III to VII used as starting materials which are known from the literature are obtained by methods known from the literature and also their preparation is described in WO 98/37075, U.S. Pat. No. 6,087,380, U.S. Pat. No. 6,414,008, U.S. Pat. No. 6,469,039, and U.S. Pat. No. 6,710,055.

Furthermore, the compounds of formula I obtained may be converted into the salts thereof, particularly for pharmaceutical use into their physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, methanesulphonic acid or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned hereinbefore, the new compounds of general formula I and their salts as prodrugs of the active substance II have valuable properties, as they are converted into thrombin-inhibiting active substance II after oral or parenteral administration. In particular, they are characterized by being well tolerated after subcutaneous administration.

For example the compounds

A=1-methyl-2-[4-(N-hydroxyamidino)-phenylaminomethyl]-benzimidazol-5-yl-carboxylic acid-(N-2-pyridyl-N-2-ethoxycarbonylethyl)-amide and B=1-methyl-2-[4-(N-methoxycarbonylamidino)-phenylaminomethyl]-benzimidazol-5-yl-carboxylic acid-(N-2-pyridyl-N-2-hydroxycarbonylethyl)-amide were investigated for their degree of tolerance when administered by subcutaneous route by comparison with active substance II:

Solutions of the test substances were each administered by subcutaneous route once a day on three successive days to two female rabbits (age: 11 to 14 weeks, weight: 2.0 to 3.5 kg). At the same time as the substances were administered a placebo solution was injected contralaterally into the same animal. The animals were killed 48 hours after the last administration and dissected. The injection sites for administering the test substances were compared histologically with the sites of the placebo injections.

In contrast to compound II, which produced clear signs of inflammation at the injection sites, compounds A and B proved to be very well tolerated locally.

In order to investigate the conversion of the prodrugs A and B into the active substance II, 1.0 ml of blood were taken from the central auricular artery of each of the test animals with K-EDTA syringes at various times after subcutaneous administration. The blood was centrifuged and the plasma was acidified with the same volume of 0.2 M hydrochloric acid. These solutions were stored at −20° C. The concentrations of the active substance II were measured using an HPLC-MS/MS apparatus (Perkin Elmer Sciex API 300 LC-MS/MS system). The detection limit was 4 ng/ml. In this way it was established that after subcutaneous injection the prodrugs A and B were converted into the active substance II in the test animals.

In view of their pharmacological properties the new compounds and the physiologically acceptable salts thereof are suitable for the prevention and treatment of venous and arterial thrombotic diseases, such as for example the treatment of deep leg vein thrombosis, for preventing reocclusions after bypass operations or angioplasty (PT(C)A), and occlusion in peripheral arterial diseases such as pulmonary embolism, disseminated intravascular coagulation, for preventing coronary thrombosis, stroke and the occlusion of shunts or stents. In addition, the compounds according to the invention are suitable for antithrombotic support in thrombolytic treatment, such as for example with rt-PA or streptokinase, for preventing long-term restenosis after PT(C)A, for preventing metastasis and the growth of clot-dependent tumors and fibrin-dependent inflammatory processes such as arthritis, for example.

The dosage required to achieve such an effect is appropriately 0.03 to 10.0 mg/kg, preferably 0.05 to 3.0 mg/kg by subcutaneous route, 0.1 to 3.0 mg/kg, preferably 0.3 to 1.0 mg/kg by intravenous route, and 0.1 to 50.0 mg/kg, preferably 0.3 to 10.0 mg/kg, by oral route, in each case administered 1 to 4 times a day. For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, water/propyleneglycol, cetylstearyl alcohol, carboxymethylcellulose or fatty substances such as hard fat or suitable mixtures thereof, to produce conventional galenic preparations such as plain or coated tablets, capsules, powders, suspensions, suppositories or injectable solutions. They are preferably incorporated in diluents such as, for example, water, water/ethanol, water/glycerol, water/sorbitol, water/polyethyleneglycol or water/propyleneglycol in order to prepare an injectable solution.

The Examples that follow are intended to illustrate the invention in more detail:

EXAMPLE 1

1-methyl-2-[4-(N-methoxycarbonylamidino)-phenylaminomethyl]-benzimidazol-5-yl-carboxylic acid-(N-2-pyridyl-N-2-hydroxycarbonylethyl)-amide A solution of 0.71 g (17.0 mmol) of lithium hydroxide-hydrate in 175 ml of water was added to a suspension of 8.50 g (15.24 mmol) of 1-methyl-2-[4-(N-methoxycarbonyl-amidino)-phenylaminomethyl]-benzimidazol-5-yl-carboxylic acid-(N-2-pyridyl-N-2-ethoxycarbonylethyl)-amide (for preparation see WO 98/37075, U.S. Pat. No. 6,087,380, U.S. Pat. No. 6,414,008, U.S. Pat. No. 6,469,039, and U.S. Pat. No. 6,710,055) in 140 ml of tetrahydrofuran, with stirring, at ambient temperature. The clear solution thus obtained was stirred for a further two hours at ambient temperature, then approx. one third of the volume was evaporated off using the rotary evaporator, the remaining solution was diluted with approx. 200 ml of water and adjusted to pH 5 to 6 with hydrochloric acid. The precipitated solid was suction filtered, dissolved in a mixture of methanol and dichloromethane (1:1), undissolved ingredients were filtered off and the filtrate was evaporated to dryness. The product thus obtained was triturated with acetone, suction filtered, washed with acetone and diethyl ether and dried.

Yield: 80.5% of theory. $C_{27}H_{27}N_7O_5$ (529.56) Mass Spectrum: $(M+H)^+=530$ $(M-H)^-=528$ $(M+Na)^+=552$ $^1$H-NMR (d6-DMSO): δ=2.61 (t, 2H); 3.58 (s, 3H); 3.77 (s,3H); 4.19 (t, 2H); 4.60 (d, 2H); 6.76 (d, 2H); 6.96 (m, 2H); 7.09 to 7.10 (m, 2H); 7.40 (d, 1H); 7.47 (s, 1H); 7.56 (t, 1H); 7.80 (d, 2H); 8.38 (m, 1H); 8.50 to 9.20 (broad d, 2H) ppm; carboxyl-H not visible.

EXAMPLE 2

1-methyl-2-[4-(N-methoxycarbonylamidino)-phenylaminomethyl]-benzimidazol-5-yl-carboxylic acid-(N-2-pyridyl-N-2-hydroxycarbonylethyl)-amide-methanesulphonate A solution of 181 mg (1.89 mmol) of methanesulphonic acid in 5 ml of methanol was added to a suspension of 1.00 g (1.89 mmol) of 1-methyl-2-[4-(N-methoxycarbonyl-amidino)-phenylaminomethyl]-benzimidazol-5-yl-carboxylic acid-(N-2-pyridyl-N-2-hydroxycarbonylethyl)-amidine in 35 ml of methanol with stirring at ambient temperature, forming a clear solution. After one hour the solution was

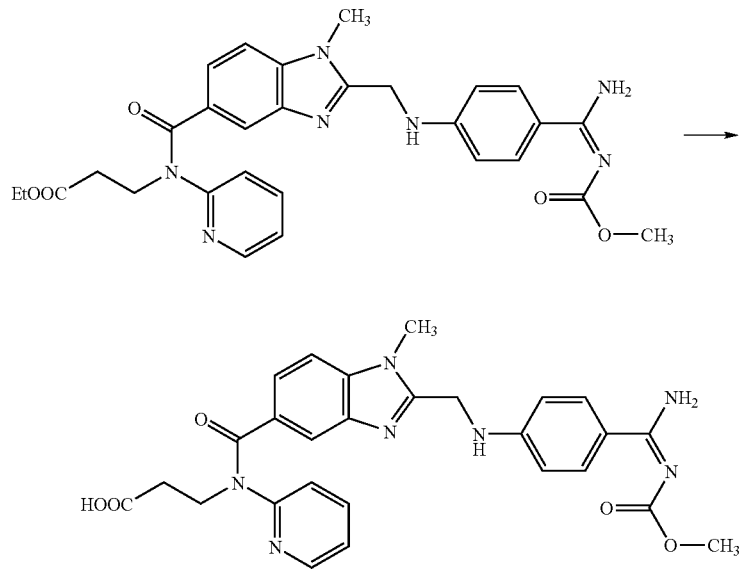

filtered, the filtrate was evaporated down to approx. 10 ml and then acetone was added dropwise until slight cloudiness set in. After another hour's stirring at ambient temperature the product precipitated was suction filtered, washed with acetone and diethyl ether and dried.

Yield: 84.7% of theory. $C_{27}H_{27}N_7O_5 \times CH_4O_3S$ (625.67) Mass Spectrum: $(M+H)^+=530$ $(M+CH_3SO_3^-)^-=624$ Melting point: from 214° C. decomposition

EXAMPLE 3

1-methyl-2-[4-(N-methoxycarbonylamidino)-phenylaminomethyl]-benzimidazol-5-yl-carboxylic acid-(N-2-pyridyl-N-2-hydroxycarbonylethyl)-amide-maleate Prepared analogously to Example 2 from 1-methyl-2-[4-(N-methoxycarbonylamidino)-phenylaminomethyl]-benzimidazol-5-yl-carboxylic acid-(N-2-pyridyl-N-2-hydroxycarbonylethyl)-amide and maleic acid.

Yield: 69.2% of theory. $C_{27}H_{27}N_7O_5 \times C_4H_4O_4$ (645.63) Mass Spectrum: $(M+H)^+=530$ $(M-H)^-=528$ $(M+C_4H_3O_4^-)^-=644$ Melting point: 179–180° C.

EXAMPLE 4

1-methyl-2-[4-(N-methoxycarbonylamidino)-phenylaminomethyl]-benzimidazol-5-yl-carboxylic acid-(N-2-pyridyl-N-2-hydroxycarbonylethyl)-amide-sodium salt A solution of 90.6 mg (2.27 mmol) of sodium hydroxide in 1.0 ml of water was added to a suspension of 1.20 g (2.27 mmol) of 1-methyl-2-[4-(N-methoxycarbonyl-amidino)-phenylaminomethyl]-benzimidazol-5-yl-carboxylic acid-(N-2-pyridyl-N-2-hydroxycarbonylethyl)-amide in 30 ml of ethanol with stirring at ambient temperature. A clear solution formed, from which the product was precipitated by slow dropwise addition of diethyl ether. After filtering, the product was washed with approx. 20 ml diethyl ether and dried at 60° C.

Yield: 72.3% of theory Melting point: amorphous $C_{27}H_{26}N_7O_5Na \times H_2O$ (569.54) Elemental Analysis:

| calculated: | C 56.94 | H 4.96 | N 17.78 |
|---|---|---|---|
| found: | C 56.68 | H 5.17 | N 17.55 |

$^1$H-NMR (d6-DMSO): δ=2.20 (t, 2H); 3.59 (s, 3H); 3.76 (s, 3H); 4.10 (t, 2H); 4.60 (d, 2H); 6.77 (d, 2H); 7.00–7.13 (m, 3H); 7.17 (d, 1H); 7.38 (d, 1H); 7.48 (s, 1H); 7.57 (t, 1H); 7.80 (d, 2H); 8.34 (m, 1H); 8.60–9.22 (d, broad, 2H) ppm.

EXAMPLE 5

1-Methyl-2-[4-(N-hydroxyamidino)-phenylaminomethyl]-benzimidazol-5-yl-carboxylic acid-(N-2-pyridyl-N-2-ethoxycarbonylethyl)-amide

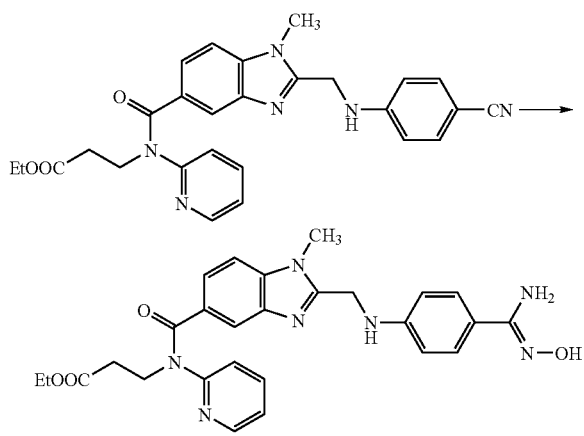

20.0 g (41.45 mmol) of 1-methyl-2-(4-cyano-phenylaminomethyl)-benzimidazol-5-yl-carboxylic acid-(N-2-pyridyl-N-2-ethoxycarbonylethyl)-amide (for preparation see WO 98/37075, U.S. Pat. No. 6,087,380, U.S. Pat. No. 6,414,008, U.S. Pat. No. 6,469,039, and U.S. Pat. No. 6,710,055) were added with stirring to a solution of HCl gas in ethanol (500 ml) saturated while cooling with ice, then the cooling bath was removed and the mixture was stirred for a further five hours. The reaction mixture was then evaporated down in vacuo using the rotary evaporator, while the temperature was kept constantly below 30° C. The residue was dissolved in 200 ml of ethanol and slowly 20.0 g (198 mmol) of triethylamine were added while cooling with ice. Then 3.75 g (54.0 mmol) of hydroxylamine-hydrochloride were added and the mixture was stirred for two hours at ambient temperature. The product precipitated was suction filtered and re-crystallized from ethanol/dichloromethane (2:1).

Yield: 61.5% of theory Melting point: 162–164° C. $C_{27}H_{29}N_7O_4$ (515.58) Mass Spectrum: $(M+H)^+=516$ $(M+Na)^+=538$ $^1$H-NMR (d6-DMSO): δ=1.12 (t, 3H); 2.69 (t, 2H); 3.76 (s, 3H); 3.98 (q, 2H); 4.22 (t, 2H); 4.52 (d, 2H); 5.55 (s, broad, 2H); 6.43 (t, 1H); 6.70 (d, 2H); 6.89 (d, 1H); 7.09 to 7.20 (m, 2H); 7.40 (m, 3H); 7.48 (s, 1H); 7.55 (t, 1H); 8.40 (m, 1H); 9.24 (s, 1H) ppm.

The following may be prepared analogously to Example 5:

1-methyl-2-[4-(N-hydroxyamidino)-phenylaminomethyl]-benzimidazol-5-yl-carboxylic acid-(N-2-pyridyl-N-2-methoxycarbonylethyl)-amide, 1-methyl-2-[4-(N-hydroxyamidino)-phenylaminomethyl]-benzimidazol-5-yl-carboxylic acid-(N-2-pyridyl-N-2-n-propyloxycarbonylethyl)-amide, 1-methyl-2-[4-(N-hydroxyamidino)-phenylaminomethyl]-benzimidazol-5-yl-carboxylic acid-(N-2-pyridyl-N-2-iso-propyloxycarbonylethyl)-amide, 1-methyl-2-[4-(N-hydroxyamidino)-phenylaminomethyl]-benzimidazol-5-yl-carboxylic acid-(N-2-pyridyl-N-2-n-butyloxycarbonylethyl)-amide, 1-methyl-2-[4-(N-hydroxyamidino)-phenylaminomethyl]-benzimidazol-5-yl-carboxylic acid-(N-2-pyridyl-N-2-isobutyloxycarbonylethyl)-amide.

EXAMPLE 6

1-Methyl-2-[4-(N-hydroxyamidino)-phenylaminomethyl]-benzimidazol-5-yl-carboxylic acid-(N-2-pyridyl-N-2-hydroxycarbonylethyl)-amide Prepared analogously to Example 1 from 1-methyl-2-[4-(N-hydroxyamidino)-phenyl-aminomethyl]-benzimidazol-5-yl-carboxylic acid-(N-2-pyridyl-N-2-ethoxycarbonylethyl)-amide.

Yield: 66.2% of theory. $C_{25}H_{25}N_7O_4$ (487.58) Mass Spectrum: $(M+H)^+=488$ $(M-H)^-=486$ $(M+Na)^+=510$

EXAMPLE 7

1-Methyl-2-[4-(N-hydroxyamidino)-phenylaminomethyl]-benzimidazol-5-yl-carboxylic acid-(N-2-pyridyl-N-2-ethoxycarbonylethyl)-amide-hydrochloride A solution of HCl in ethanol was produced by stirring 152 mg (1.94 mmol) of acetylchloride into 5.0 ml of ethanol. The solution obtained was added at ambient temperature to a solution of 1.0 g (1.94 mmol) of 1-methyl-2-[4-(N-hydroxyamidino)-phenylaminomethyl]-benzimidazol-5-ylcarboxylic acid-(N-2-pyridyl-N-2-ethoxycarbonylethyl)-amide in 50 ml of absolute ethanol, then it was evaporated down to a volume of approx. 10 ml using a rotary evaporator and then ethyl acetate was added dropwise with stirring until slight cloudiness could be observed. The mixture was stirred for approx. a further 15 hours, then the product precipitated was suction filtered, washed with diethyl ether and dried.

Yield: 78.3% of theory. Melting point: 155–157° C. Mass Spectrum: $(M+H)^+=516$ $(M+Na)^+=538$ $C27H29N7O4 \times HCl \times H2O$ (570.05) Elemental Analysis:

| calculated: | C 56.89 | H 5.66 | N 17.20 | Cl 6.22 |
| --- | --- | --- | --- | --- |
| found: | C 56.80 | H 5.67 | N 17.06 | Cl 6.25 |

EXAMPLE 8

1-Methyl-2-[4-(N-hydroxyamidino)-phenylaminomethyl]-benzimidazol-5-yl-carboxylic acid-(N-2-pyridyl-N-2-ethoxycarbonylethyl)-amide-maleate 1.0 g (1.94 mmol) of 1-methyl-2-[4-(N-hydroxyamidino)-phenylaminomethyl]-benzimidazol-5-yl-carboxylic acid-(N-2-pyridyl-N-2-ethoxycarbonylethyl)-amide was dissolved with heating in 100 ml of absolute ethanol and 225 mg (1.94 mmol) of maleic acid were added. The solution was then evaporated down to a volume of about 15 ml and ethyl acetate was added dropwise at ambient temperature until slight cloudiness could be detected. After stirring overnight the precipitated product was suction filtered, washed with diethyl ether and dried.

Yield: 61.0% of theory. Melting point: amorphous. $C27H29N7O4 \times C4H4O4$ Mass Spectrum: $(M+H)^+=516$ $(M+Na)^+=538$

EXAMPLE 9

1-Methyl-2-[4-(N-hydroxyamidino)-phenylaminomethyl]-benzimidazol-5-yl-carboxylic acid-(N-2-pyridyl-N-2-ethoxycarbonylethyl)-amide-methanesulphonate Prepared analogously to Example 8 from 1-methyl-2-[4-(N-hydroxyamidino)-phenylaminomethyl]-benzimidazol-5-yl-carboxylic acid-(N-2-pyridyl-N-2-ethoxycarbonylethyl)-amide and methanesulphonic acid.

Yield: 67.4% of theory. Melting point: 128–130° C. Mass Spectrum: $(M+H)^+=516$ $(M+Na)^+=538$

EXAMPLE 10

Dry Ampoule Containing 75 mg of Active Substance Per 10 ml

Composition:

| Active substance | 75.0 mg |
| --- | --- |
| Mannitol | 50.0 mg |
| water for injections | ad 10.0 ml |

Preparation:

Active substance and mannitol are dissolved in water. After packaging the solution is freeze-dried. To produce the solution ready for use, the product is dissolved in water for injections.

EXAMPLE 11

Dry Ampoule Containing 35 mg of Active Substance Per 2 ml

Composition:

| Active substance | 35.0 mg |
| --- | --- |
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 12

Tablet Containing 50 mg of Active Substance

Composition:

| | | |
| --- | --- | --- |
| (1) | Active substance | 50.0 mg |
| (2) | Lactose | 98.0 mg |
| (3) | Maize starch | 50.0 mg |
| (4) | Polyvinylpyrrolidone | 15.0 mg |
| (5) | Magnesium stearate | 2.0 mg |
| | | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

EXAMPLE 13

Tablet Containing 350 mg of Active Substance

Composition:

| | | |
| --- | --- | --- |
| (1) | Active substance | 350.0 mg |
| (2) | Lactose | 136.0 mg |
| (3) | Maize starch | 80.0 mg |
| (4) | Polyvinylpyrrolidone | 30.0 mg |
| (5) | Magnesium stearate | 4.0 mg |
| | | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

EXAMPLE 14

Capsules Containing 50 mg of Active Substance

Composition:

| | | |
|---|---|---|
| (1) | Active substance | 50.0 mg |
| (2) | Dried maize starch | 58.0 mg |
| (3) | Powdered lactose | 50.0 mg |
| (4) | Magnesium stearate | 2.0 mg |
| | | 160.0 mg |

Preparation:

(1) is triturated with (3). This trituration is added to the mixture of (2) and (4) with vigorous mixing.

This powder mixture is packed into size 3 hard gelatin capsules in a capsule filling machine.

EXAMPLE 15

Capsules Containing 350 mg of Active Substance

Composition:

| | | |
|---|---|---|
| (1) | Active substance | 350.0 mg |
| (2) | Dried maize starch | 46.0 mg |
| (3) | Powdered lactose | 30.0 mg |
| (4) | Magnesium stearate | 4.0 mg |
| | | 430.0 mg |

Preparation:

(1) is triturated with (3). This trituration is added to the mixture of (2) and (4) with vigorous mixing.

This powder mixture is packed into size 0 hard gelatin capsules in a capsule filling machine.

EXAMPLE 16

Suppositories Containing 100 mg of Active Substance
1 suppository contains:

| | |
|---|---|
| Active substance | 100.0 mg |
| Polyethyleneglycol (M.W.1500) | 600.0 mg |
| Polyethyleneglycol (M.W.6000) | 460.0 mg |
| Polyethylenesorbitan monostearate | 840.0 mg |
| | 2000.0 mg |

What is claimed is:

1. A pharmaceutical composition comprising:
a compound of the formula

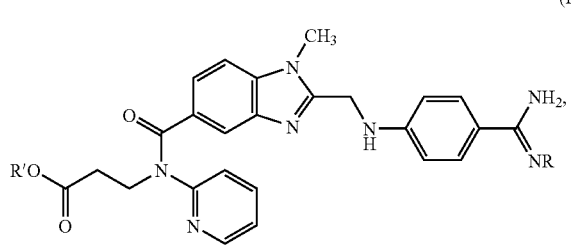

(I)

wherein (i) R' denotes a hydrogen atom and R denotes a methoxycarbonyl group, or (ii) R' denotes a hydrogen atom or a $C_{1-6}$-alkyl group and R denotes a hydroxy group, and wherein the alkyl groups which contain more than 2 carbon atoms also include the branched isomers thereof, or a tautomer or pharmaceutically acceptable salt thereof, the pharmaceutical composition adapted for administration to a patient in an amount of approximately 0.03 mg to approximately 10.0 mg per kilogram of patient weight.

2. The pharmaceutical composition according to claim 1, wherein
   a) R' denotes a hydrogen atom and R denotes a methoxycarbonyl group or
   b) R' denotes a hydrogen atom or a $C_{1-3}$-alkyl group and R denotes a hydroxy group, while the $C_3$-alkyl group also includes an isopropyl group,
   or a tautomer or pharmaceutically acceptable salt thereof.

3. The pharmaceutical composition according to claim 1, wherein the compound comprises 1-Methyl-2-[4-(N-hydroxyamidino)-phenylaminomethyl]-benzimidazol-5-yl-carboxylic acid-(N-2-pyridyl-N-2-ethoxycarbonylethyl)-amide, or a tautomer or pharmaceutically acceptable salt thereof.

4. The pharmaceutical composition according to claim 1, wherein the compound comprises 1-Methyl-2-[4-(N-methoxycarbonylamidino)-phenylaminomethyl]-benzimidazol-5-yl-carboxylic acid-(N-2-pyridyl-N-2-hydroxycarbonylethyl)-amide, or a tautomer or pharmaceutically acceptable salt thereof.

5. The pharmaceutical composition according to claim 1, wherein the compound comprises the maleate, the hydrochloride, or the methanesulphonate of 1-methyl-2-[4-(N-hydroxyamidino)-phenylaminomethyl]-benzimidazol-5-yl-carboxylic acid-(N-2-pyridyl-N-2-ethoxycarbonylethyl)-amide.

6. The pharmaceutical composition according to claim 1, wherein the compound comprises the maleate, the methanesulphonate, or the sodium salt of the compound 1-methyl-2-[4-(N-methoxycarbonylamidino)-phenylaminomethyl]-benzimidazol-5-yl-carboxylic acid-(N-2-pyridyl-N-2-hydroxycarbonylethyl)-amide.

7. The pharmaceutical composition according to claim 1, further comprising one or more inert carriers and/or diluents.

8. The pharmaceutical composition according to claim 1, packaged in an ampoule or capsule.

9. The pharmaceutical composition according to claim 1, formed as a tablet.

10. A method for treating thrombus formation comprising:
    administering an antithrombotic amount of a pharmaceutical composition comprising:
    a compound of the formula

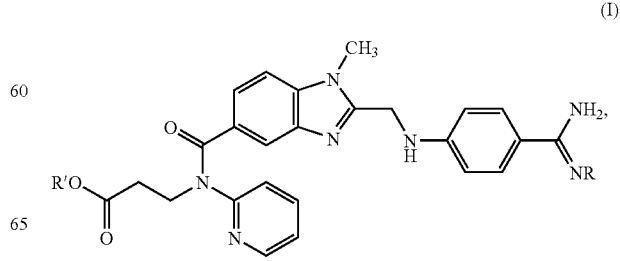

(I)

wherein (i) R' denotes a hydrogen atom and R denotes a methoxycarbonyl group, or (ii) R' denotes a hydrogen atom or a $C_{1-6}$-alkyl group and R denotes a hydroxy group, and wherein the alkyl groups which contain more than 2 carbon atoms also include the branched isomers thereof, or a tautomer or pharmaceutically acceptable salt thereof, the pharmaceutical composition adapted for administration to a patient in an amount of approximately 0.03 mg to approximately 10.0 mg per kilogram of patient weight.

11. The method according to claim 10, wherein
a) R' denotes a hydrogen atom and R denotes a methoxycarbonyl group or
b) R' denotes a hydrogen atom or a $C_{1-3}$-alkyl group and R denotes a hydroxy group, while the $C_3$-alkyl group also includes an isopropyl group,
or a tautomer or pharmaceutically acceptable salt thereof.

12. The method according to claim 10, wherein the compound comprises 1-Methyl-2-[4-(N-hydroxyamidino)-phenylaminomethyl]-benzimidazol-5-yl-carboxylic acid-(N-2-pyridyl-N-2-ethoxycarbonylethyl)-amide, or a tautomer or pharmaceutically acceptable salt thereof.

13. The method according to claim 10, wherein the compound comprises 1-Methyl-2-[4-(N-methoxycarbonylamidino)-phenylaminomethyl]-benzimidazol-5-yl-carboxylic acid-(N-2-pyridyl-N-2-hydroxycarbonylethyl)-amide, or a tautomer or pharmaceutically acceptable salt thereof.

14. The method according to claim 10, wherein the compound comprises the maleate, the hydrochloride, or the methanesulphonate of 1-methyl-2-[4-(N-hydroxyamidino)-phenylaminomethyl]-benzimidazol-5-yl-carboxylic acid-(N-2-pyridyl-N-2-ethoxycarbonylethyl)-amide.

15. The method according to claim 10, wherein the compound comprises the maleate, the methanesulphonate, or the sodium salt of the compound 1-methyl-2-[4-(N-methoxycarbonylamidino)-phenylaminomethyl]-benzimidazol-5-yl-carboxylic acid-(N-2-pyridyl-N-2-hydroxycarbonylethyl)-amide.

16. The method according to claim 10, wherein the pharmaceutical composition further comprising one or more inert carriers and/or diluents.

17. The method according to claim 10, wherein the pharmaceutical composition is packaged in an ampoule or capsule.

18. The method according to claim 10, wherein the pharmaceutical composition is formed as a tablet.

* * * * *